United States Patent [19]

Bömches et al.

[11] Patent Number: 4,507,482

[45] Date of Patent: Mar. 26, 1985

[54] PURIFICATION OF MEFLOQUIN HYDROCHLORIDE

[75] Inventors: Helmut Bömches, Aesch; Bruno Hardegger, Riehen, both of Switzerland

[73] Assignee: Hoffmann-La Roche Inc., Nutley, N.J.

[21] Appl. No.: 481,691

[22] Filed: Apr. 4, 1983

[30] Foreign Application Priority Data

Apr. 14, 1982 [CH] Switzerland .......................... 2256/82

[51] Int. Cl.$^3$ ............................................. C07D 403/02
[52] U.S. Cl. ..................................................... 546/176
[58] Field of Search ........................................ 546/176

[56] References Cited

PUBLICATIONS

Chien et al., J. Med. Chem. (1976), vol. 19, pp. 170–172.

*Primary Examiner*—Glennon H. Hollrah
*Assistant Examiner*—D. B. Springer
*Attorney, Agent, or Firm*—Jon S. Saxe; Bernard S. Leon; William G. Isgro

[57] ABSTRACT

A method for obtaining mefloquin hydrochloride, erythro-α-2-piperidyl-2,8-bis-(trifluoromethyl)-4-quinolinemethanol hydrochloride, from mixtures of erythro-and threo-α-2-piperidyl-2,8-bis-(trifluoromethyl)-4-quinolinemethanol hydrochloride by treatment with aqueous methanol or ethanol. The thermodynamically most stable form is obtained by treatment with an alcohol/water mixture for a long period of time.

8 Claims, 4 Drawing Figures

Fig. 2 MEFLOQUIN HYDROCHLORIDE, MODIFICATION B

Fig. 3 MEFLOQUIN HYDROCHLORIDE, MODIFICATION C

MEFLOQUIN HYDROCHLORIDE, MODIFICATION D

PURIFICATION OF MEFLOQUIN HYDROCHLORIDE

BRIEF SUMMARY OF THE INVENTION

The invention relates to a method for obtaining erythro-α-2-piperidyl-2,8-bis-(trifluoromethyl)-4-quinolinemethanol hydrochloride from mixtures of erythro- and threo-α-2-piperidyl-2,8-bis-(trifluoromethyl)-4-quinolinemethanol hydrochloride, which method comprises treating said mixtures with an aqueous alcohol.

In another aspect, the invention relates to erythro-α-2-piperidyl-2,8-bis-(trifluoromethyl)-4-quinolinemethanol hydrochloride in its thermodynamically most stable form.

In yet another aspect, the invention relates to a pharmaceutical composition comprising an effective amount of erythro-α-2-piperidyl-2,8-bis-(trifluoromethyl)-4-quinolinemethanol hydrochloride in its thermo-dynamically most stable form and an inert carrier material.

DETAILED DESCRIPTION OF THE INVENTION

Mefloquin, erythro-α-2-piperidyl-2,8-bis-(trifluoromethyl)-4-quinolinemethanol, is a valuable active substance for the treatment of even the chloroquine-resistant form of malaria, see, for example, Antimicrobial Agents Chemother. 9, 384 [1976]; several processes for its manufacture are known (J. Med. Chem. 14, 926 [1971]; DOS No. 28 06 909; DOS No. 29 40 443). In the processes for the preparation of mefloquin in which the last step comprises the catalytic hydrogenation of 2-pyridyl 2,8-bis-(trifluoromethyl)-4-quinolyl ketone, there always results in addition to the biologically active erythro form a smaller amount (about 5–15%) of the inactive and therefore undesired threo form. The separation of this mixture and the purification of the erythro form has hitherto been possible only by a relatively costly method which involved the repeated recrystallization from an acetone/alcohol mixture, washing with acetone and crystallization from acetonitrile.

It has now been found that the separation of the threo form from the erythro form and the purification of the latter can be achieved in a surprisingly effective manner by treating the mixture of erythro- and threo-α-2-piperidyl-2,8-bis-(trifluoromethyl)-4-quinolinemethanol hydrochloride, resulting from the hydrogenation of the ketone precursor with aqueous methanol or ethanol whereby the threo form passes into solution and the erythro form remains behind. Residues of the threo compound as well as other byproducts can be removed by additional purification, for example, by treatment with acetone, that is, via an acetone complex.

Figure 1:
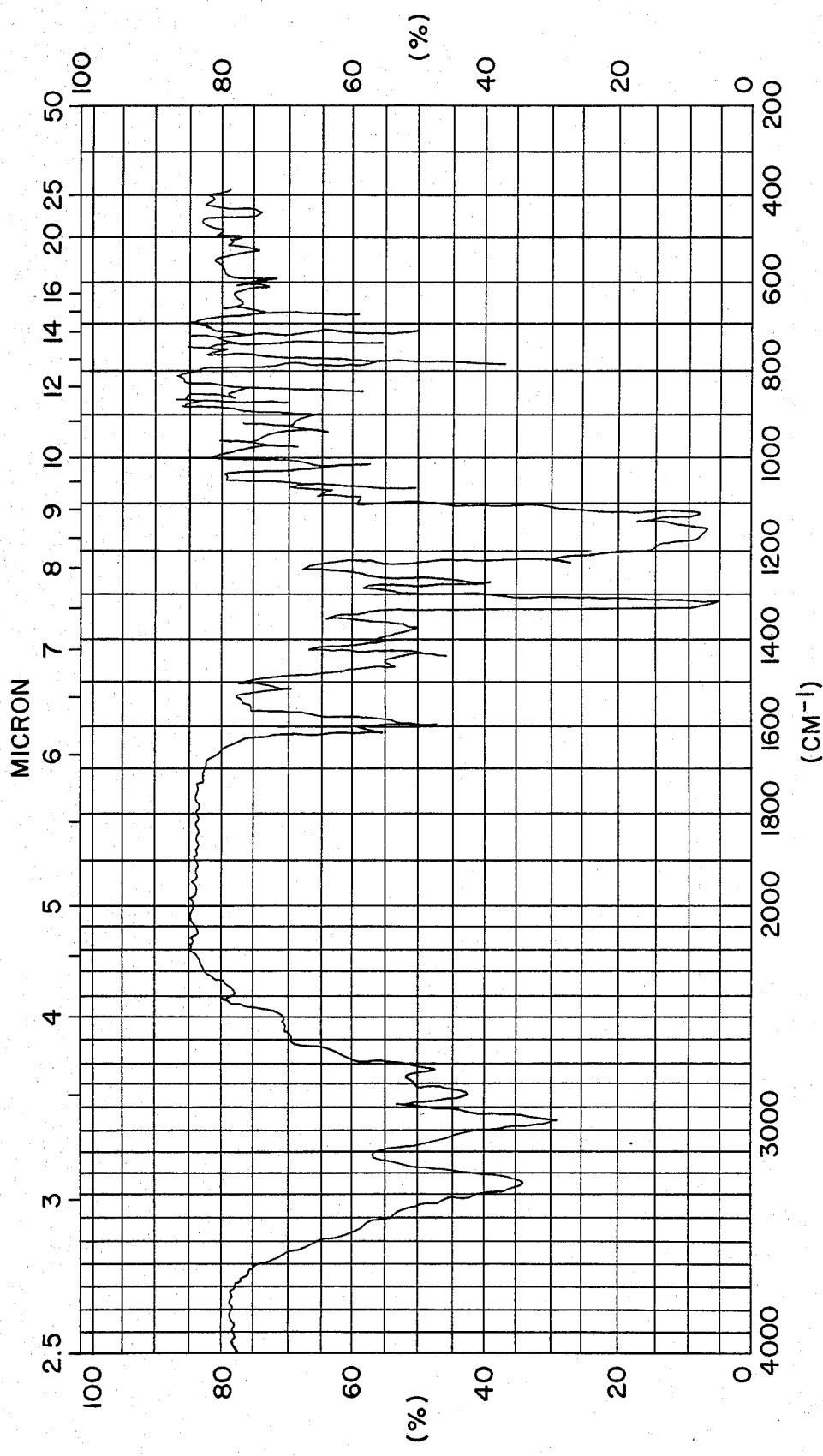
Figure 2:
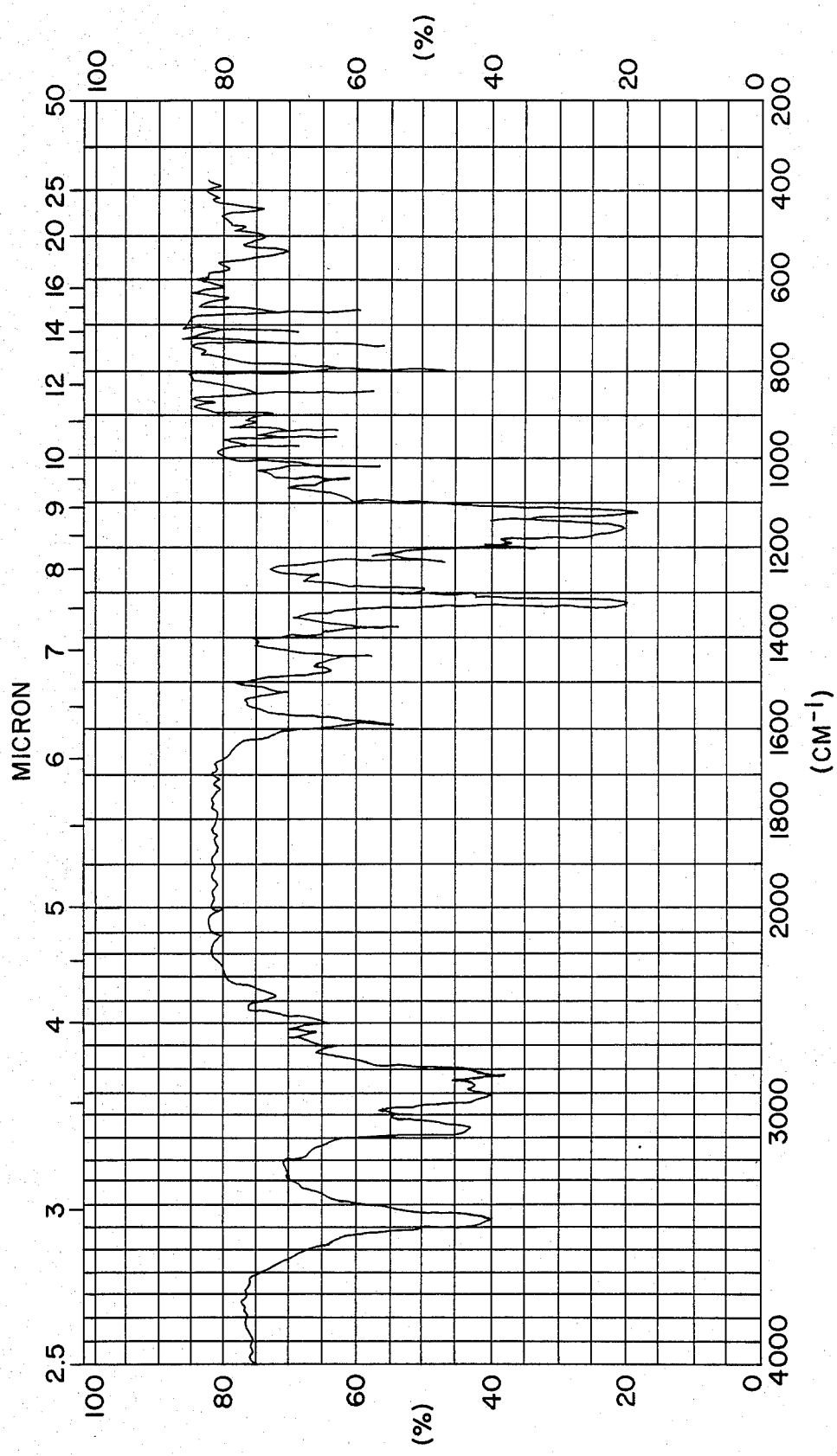
Figure 3:
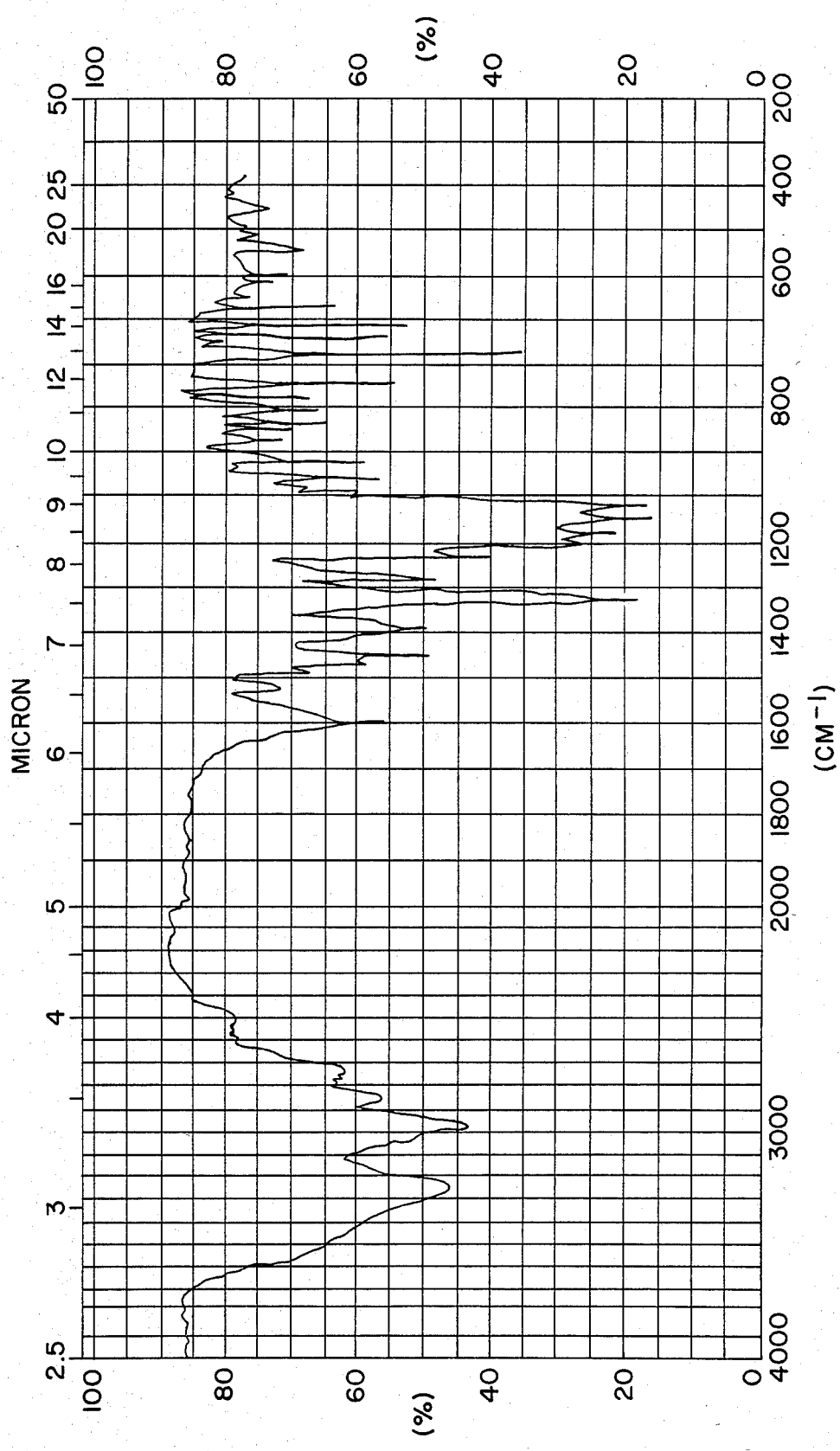
Figure 4:
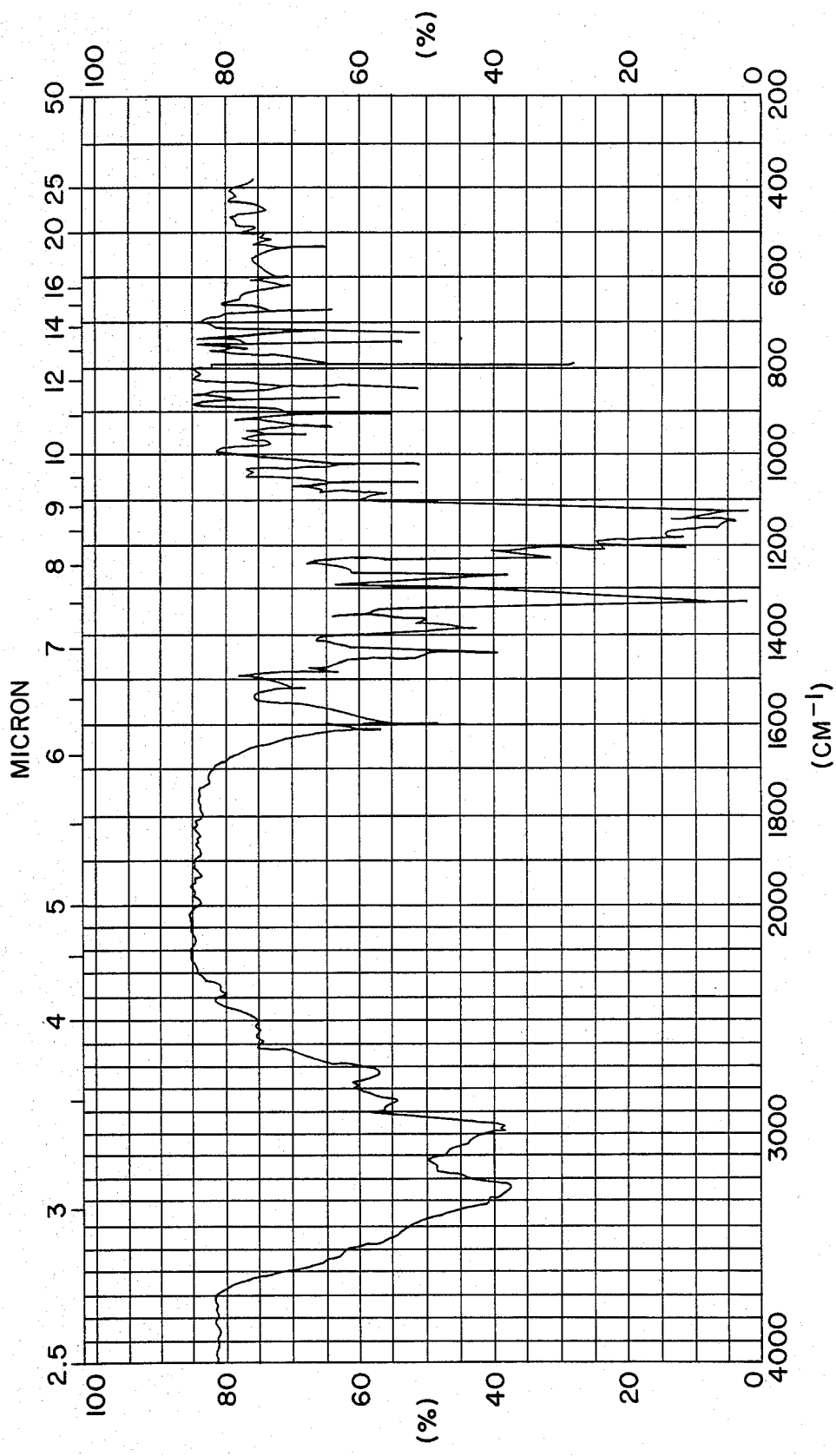

It has also been found that pure mefloquin hydrochloride occurs in various forms which can be differentiated from one another by crystallographical means or on the basis of their IR spectra. Thus, in the purification by means of acetonitrile there is obtained a form A, mefloquin.HCl, which is characterized by IR spectrum A (see FIG. 1), while by the brief treatment with acetone there is obtained form B, mefloquin.HCl.acetone, and with water/alcohol mixtures there is obtained form C, mefloquin.HCl.½H$_2$O (see IR spectra B and C, FIGS. 2 and 3 respectively) In the case of longer treatment of mefloquin hydrochloride with alcohol/water mixtures there is formed form D, mefloquin.HCl.½H$_2$O, which is the thermodynamically most stable form (see IR spectrum D, FIG. 4). A comparison of the IR spectra shows that the differences lie in the wavelength ranges 900–960 and 1100 –1200 cm$^{-1}$.

The present invention relates to a method for obtaining erythro-α-2-piperidyl-2,8-bis-(trifluoromethyl)-4-quinolinemethanol hydrochloride from mixtures of erythro- and threo-α-2-piperidyl-2,8-bis-(trifluoromethyl)-4-quinolinemethanol hydrochloride especially from those which are obtained in the hydrogenation of 2-pyridyl 2,8-bis-(trifluoromethyl)-4-quinolyl ketone, which method comprises treating said mixtures with aqueous methanol or ethanol.

The invention also relates to erythro-α-2-piperidyl-2,8-bis-(trifluoromethyl)-4-quinolinemethanol hydrochloride in its thermodynamically most stable form, i.e. crystallized from alcohol/water mixtures, characterized by its IR spectrum, as well as its preparation by treating mefloquin hydrochloride, which is present at least partially in another form, with an alcohol/water mixture for a long period of time. In the treatment of mixtures of erythro- and threo-α-2-piperidyl-2,8-bis-(trifluoromethyl)-4-quinolinemethanol with aqueous methanol or ethanol the threo form passes into solution. The treatment can be carried out by stirring at room temperature for 30 minutes to several hours, or while heating to about 80° C. and subsequently cooling to about 5° C. (in order to increase the yield). The amount of water in the solvent mixture can be varied by wide limits; however, conveniently lies between 60 and 95 vol.%, preferably between 70 and 90 vol.%. In the working-up of methanolic reaction solutions which are obtained, for example, in the catalytic hydrogenation of 2-pyridyl 2,8-bis-(trifluoromethyl)-4-quinolyl ketone in methanol containing hydrochloric acid, conveniently a portion of the methanol is first removed and then an appropriate amount of water is added. The thus-obtained mefloquin hydrochloride (crude) is washed with cold water and is then practically free from the undesired threo form.

By working-up the mother liquors according to the previously described method in combination with the method of acetone complex formation there can be achieved in principle a complete separation of erythro and threo form.

Chemically, the thus-obtained crude is practically uniform, but in general it exists neither in a uniform crystal form nor in the thermodynamically most stable form. In order to achieve this, the crude is stirred for a longer time, that is, at least about 6 hours to about 12 hours, with an alcohol, for example, methanol, ethanol, isopropanol, or the like, preferably methanol, in the presence of water, about 50–80 vol. %. The treatment can be carried out at room temperature or while cooling to temperatures slightly above 0° C. in order to increase the yield.

The Examples which follow further illustrate the invention. All temperatures are in degrees Centigrade unless otherwise stated.

EXAMPLE 1

50 kg of 2-pyridyl 2,8-bis-(trifluoromethyl)-4-quinolyl ketone were dissolved in 550 l of methanol while heating to 56°–58° C. The solution was cooled to 25° C. and combined with a pre-hydrogenated suspension of 2.5 kg of platinum dioxide and 2.5 kg of hydrogenation carbon in 210 l of methanol and 14.1 of 33% iron-free hydrochloric acid (d=1.170). The mixture was hydrogenated for 6–8 hours under normal pressure at a maximum internal temperature of 30° C. until the hydrogen uptake was complete.

The mixture was filtered, the methanolic solution was concentrated under reduced pressure to a volume of 100–150 l, treated with 250–350 l of water and subsequently again brought to a volume of 300–350 l under reduced pressure. It was stirred for 1 hour while slowly heating to 80° C., then stirred at this temperature for an additional 30 minutes, cooled to 5° C. and stirred for an additional hour. The suspension was centrifuged. The still moist centrifuged material or residue was introduced into 250 l of water of 5° C. and stirred for 15 minutes. The mixture was again centrifuged, the centrifuged material or residue was rinsed several times, in each case, with 20 l of water of 5° C., centrifuged well and dried for 12 hours at 70° C. under reduced pressure. There were obtained 46–48 kg (82.1–85.6% of theory) of crude mefloquin hydrochloride which was practically free from the undesired threo form and which was purified further as follows:

A suspension of 150 kg of crude mefloquin hydrochloride in 75 l of absolute ethanol and 425 l of acetne was brought to reflux temperature while stirring within 1 hour and held at this temperature for 30 minutes. The mixture was cooled to 20° C., treated with 50 l of ethanol/acetate (42.5:7.5), cooled to about 0° C. while stirring and stirred at this temperature for another 4 hours. The suspension was centrifuged, the well centrifuged material was rinsed several times, in each case, with 15 l of acetone at 5° C. and dried in a vacuum drier at 70° C. There were obtained 136–142 kg of purified mefloquin hydrochloride.

100 Kg of thus-purified mefloquin hydrochloride in 300 l of methanol were heated to reflux. The hot solution was introduced into 1180 l of water and stirred for at least 4 hours. While cooling to 2° C. it was then stirred for at least another 6 hours. After centrifugation and two-fold rinsing of the centrifuged material, in each case, with 15 l of water of 5° C., it was dried in a vacuum drier at 70° C. There were obtained 80–85 kg of pure mefloquin hydrochloride in its thermodynamically most stable form accruing from aqueous media, m.p. 255°–259° C. (see IR spectrum D, FIG. 4). The yield of pure product can be increased further by extracting the mother liquor with methylene chloride and working-up the organic phase in the laboratory.

EXAMPLE 2

120 Kg of 2-pyridyl 2,8-bis-(trifluoromethyl)-4-quinolyl ketone were suspended in 196 l of methanol and 17.4 kg of 30% hydrochloric acid and the suspension was combined with a pre-hydrogenated suspension of 9 kg of platinum dioxide and 9 kg of hydrogenation carbon in 300 l of methanol. The mixture was hydrogenated for 10 hours under 0.1–0.5 bar gauge pressure at a maximum internal temperature of 20° C. until the hydrogen uptake was complete.

The mixture was filtered, the kettle and filter were rinsed with 80 ml of methanol, the methanolic solution was concentrated under reduced pressure to a volume of 100–150 l and treated with 800–880 l of water. The resulting mixture was stirred for 1 hour while slowly heating to 80° C., then stirred at this temperature for another 30 minutes, cooled to 5° C. and stirred for another hour. The suspension was centrifuged, the centrifuged material was rinsed several times with in each case 30 l of water of 5° C., centrifuged well and dried for 12 hours at 80° C. under reduced pressure. There were obtained 110–115 kg of crude mefloquin hydrochloride which was practically free from the undesired threo form and which was purified further as described in Example 1.

EXAMPLE 3

| Tablets containing | |
|---|---|
| Mefloquin hydrochloride, modification D | 274.12 mg |
| Cellulose | 100.0 mg |
| D-Mannitol | 87.88 mg |
| Polyvinylpyrrolidone | 15.0 mg |
| Sodium carboxymethyl starch | 10.0 mg |
| Talc | 10.0 mg |
| Magnesium stearate | 3.0 mg |
| | 500.0 mg |

Preparation

A sieved mixture of mefloquin hydrochloride (modification D), D-mannitol and a portion of the cellulose (microcrystalline) was moistened with an aqueous solution of polyvinylpyrrolidone and kneaded. The homogeneous mixture was then granulated, dried and sieved. To the granulate there was added a sieved mixture of cellulose (microcrystalline), sodium carboxymethyl starch, talc and magnesium stearate. The ingredients were mixed to yield a homogeneous mixture which was pressed into tablets of 500 mg each.

We claim:

1. A method for obtaining erythro-α-2-piperidyl-2,8-bis-(trifluoromethyl)-4-quinolinemethanol hydrochloride from mixtures of erythro- and threo-α-2-piperidyl-2,8-bis-(trifluoromethyl)-4-quinolinemethanol hydrochloride, which method comprises treating said mixtures with an aqueous alcohol, wherein the alcohol is selected from the group consisting of methanol, ethanol and isopropanol, and, thereafter, separating the erythro-α-2-piperidyl-2,8-bis-(trifluoromethyl)-4-quinolinemethanol hydrochloride.

2. A method in accordance with claim 1, wherein the alcohol is methanol or ethanol.

3. A method in accordance with claim 2, wherein the mixture is one which has been obtained by hydrogenating 2-pyridyl 2,8-bis-(trifluoromethyl)-4-quinolyl ketone.

4. A method in accordance with claim 2, wherein the aqueous alcohol contains about 70–90 vol. % water.

5. A method for preparing erythro-α-2-piperidyl-2,8-bis-(trifluoromethyl)-4-quinolinemethanol hydrochloride essentially free from the threo form, which method comprises treating erythro-α-2-piperidyl-2,8-bis-(trifluoro-methyl)-4-quinolinemethanol hydrochloride, which is present at least partially in another form, with an alcohol/water mixture, wherein the alcohol is selected from the group consisting of methanol, ethanol and isopropanol, and, thereafter, separating the erythro-α-2-piperidyl-2,8-bis-(trifluoromethyl)-4-quinolinemethanol hydrochloride.

6. A method in accordance with claim 5, wherein the treatment is carried out for at least 6 hours.

7. A method in accordance with claim 6, wherein the treatment is carried out at a temperature in the range of 0° C. to room temperature.

8. Erythro-α-2-piperidyl-2,8-bis-trifluoromethyl-4-quinolinemethanol hydrochloride whose I. R. corresponds to FIG. 4, modification D, and is essentially free from the threo from, which is prepared by treating erythro-α-2-piperidyl-2,8-bis(trifluoromethyl)-4-quinolinemethanol hydrochloride, which is present at least partially in another form, with an alcohol/water mixture, wherein the alcohol is selected from the group consisting of methanol, ehtanol and isopropanol, and thereafter, separating the erythro-α-2-piperidyl-2,8-bis-(trifluoromethyl)-4-quinolinemethanol hydrochloride.

* * * * *